United States Patent [19]

Meilland, deceased

[11] Patent Number: Plant 7,334

[45] Date of Patent: Sep. 25, 1990

[54] ROSE PLANT—MEICHEVIL VARIETY

[75] Inventor: Marie-Louise Meilland, deceased, late of Antibes, by Jean-pierre Le Naour, Legal Representative

[73] Assignee: The Conard-Pyle Company, West Grove, Pa.

[21] Appl. No.: 321,142

[22] Filed: Mar. 9, 1989

[51] Int. Cl.[5] ..... A01H 5/00

[52] U.S. Cl. ..... Plt./28

[58] Field of Search ..... Plt./25, 28

[56] References Cited

U.S. PATENT DOCUMENTS

P.P. 2,945 12/1969 Swim et al. ..... Plt. 22

P.P. 5,636 1/1986 Jelly ..... Plt. 26

*Primary Examiner*—Howard J. Locker

*Attorney, Agent, or Firm*—Burns, Doane, Swecker & Mathis

[57] ABSTRACT

A new and distinct variety of Floribunda rose plant is provided which abundantly forms attractive semi-double blossoms. These blossoms are cardinal in coloration and several blossoms commonly are borne per stem. Such blossoms are exceptionally long lasting. The plant exhibits a semi-erect growth habit, forms vigorous vegetation and is well suited for cut flower production. Additionally, the plant is not particularly affected by cryptogamic diseases.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the Pink Garnette variety (U.S. Plant Pat. No. 1,120). The male parent (i.e., the pollen parent) was the product of the pollination of the Misty Pink variety (U.S. Plant Pat. No. 2,945) by an unnamed seedling (non-patented in the United States). The parentage of the new variety can be summarized as follows:

Pink Garnette × [Misty Pink × Unnamed Seedling].

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) forms in abundance attractive semi-double cardinal blossoms which exhibit an exceptionally long vase life,
(b) exhibits a semi-erect growth habit,
(c) exhibits vigorous vegetation, and
(d) is particularly well suited for cut flower production.

The long vase life of the blossoms is particularly noteworthy.

The new variety well meets the needs of the horticultural industry for all uses and is particularly well suited for cut flower production.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meichevil variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa indicia* understock and growing in a greenhouse at Cap d'Antibes, France.

FIG. 1 illustrates a specimen of a young shoot;

DETAILED DESCRIPTION

Figures 2, 3, 4, 5, 6, 7, 8, 9, 10, 11, 12, 13, 14, 15, 16:
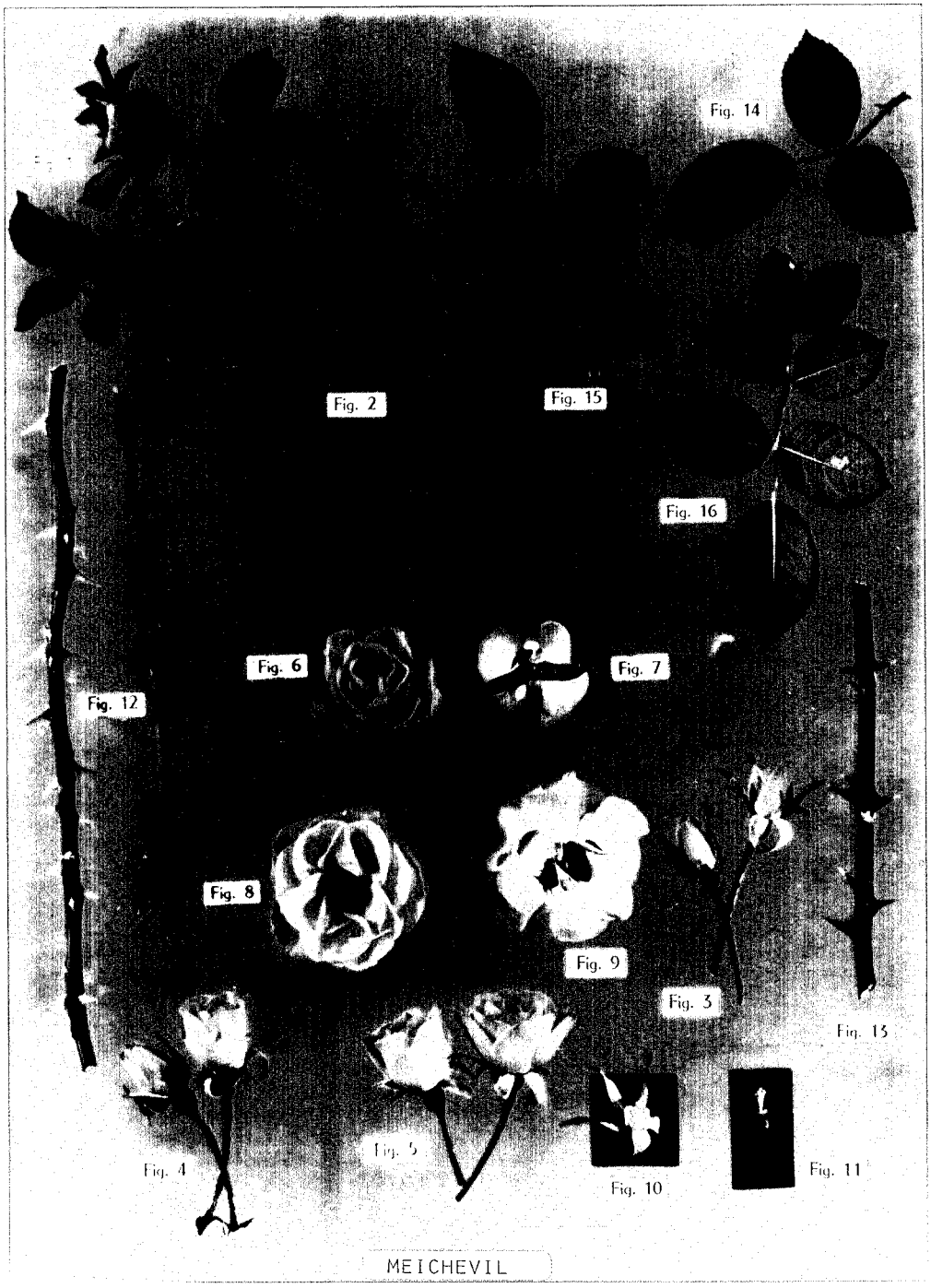
FIG. 2 illustrates specimens of four floral buds before the opening of the sepals.
FIG. 3 illustrates specimens of two floral buds at the opening of the sepals.
FIG. 4 illustrates specimens of two floral buds at the opening of the petals.
FIG. 5 illustrates specimens of two flowers in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates specimens of two flowering stems.
FIG. 13 illustrates a specimen of a main branch.
FIG. 14 illustrates a specimen of a leaf with three leaflets — plan view — upper surface.
FIG. 15 illustrates a specimen of a leaf with five leaflets — plan view — upper surface.
FIG. 16 illustrates a specimen of a leaf with seven leaflets — plan view — under surface.

The chart used in the identification of the colors is that of The Royal Horticultural Society (R.H.S. Colour Chart). The description is based on two year old plants made during September while budded on *Rosa indicia* understock and growing in a greenhouse at Cap d'Antibes, France. The coloration in common terms precedes reference to the chart.

Class: Floribunda.

Plant:

*Height.*—Plants when pruned to a height of 85 cm. produce floral stems having a length of approximately 30 to 50 cm. When grown in the field at Wasco, Calif., one-year old plants from which one cutting of blossoms has been taken, commonly will assume a height of approximately 1.3 m. at the end of the growing season.

*Habit.*—Semi-erect.

Branches:

*Color.*—Young stems: medium green, Yellow-Green Group 146B. Adult wood: medium green, Green Group 137B.

*Thorns.*—Size: medium. Quantity: few. Color: reddish on young stems and pinkish-greenish on adult wood changing to tan.

Leaves:

*Stipules.*—Adnate, pectinate, wide and linear.

*Petioles.*—Upper surface: striped reddish brown on young foliage and medium green on adult foliage with more or less glandular edges. Under surface: light green, bear a few prickles.

*Leaflets.*—Number: 3, 5 (most often), and 7. Shape: usually oval. Serration: simple and regular. Texture: leather. General appearance: dense and semi-dull foliage. Color (young foliage): Upper surface: medium green, Yellow-Green Group 146B, more or less stained reddish brown. Under surface: medium green, Yellow-Green Group 146B, more or less stained reddish. Color (adult foliage): Upper surface: dark green, Yellow-Green Group 147A. Under surface: medium green, Yellow-Green Group 147B.

Inflorescence:

*Number of flowers.*—1 to 6 per stem, and commonly 3 to 4 per stem.

*Peduncle.*—Straight, rigid, light green in coloration, and bears glandular prickles. The length is approximately 4 to 5 cm. on average.

*Sepals.*—Upper surface: greenish and tomentose. Under surface: light green and the outer sepals have glandular edges which are more or less appendiculate.

*Buds.*—Shape: conical. Length: approximately 2 to 2.5 cm. on average from the calyx before the opening of the sepals. Size: small. Color upon opening: Upper surface: dark cardinal, Red Group 53C. Under surface: strong cardinal, Red Group 53D and lighter at the center of the petals.

*Flower.*—Shape: hollow cup-like and semi-double. Diameter: approximately 6.5 to 7 cm. on average. Color (when opening begins): Upper surface: dark cardinal, Red Group 53C. Under surface: strong cardinal, Red Group 53D and lighter at the center of the petals. Color (when blooming): Upper surface: dark cardinal, Red Group 53C. Under surface: strong cardinal, Red Group 53D and lighter at the center of the petals. Color (at end of opening): Upper surface: dark cardinal, Red Group 53D. under surface: strong cardinal, Red Group 53D and lighter at the center of the petals. Fragrance: none. Lasting quality: very long. Petal number: approximately 16 to 22 on average. Texture: consistent. Petal drop: good. Stamen number: approximately 57 to 63 on average. Anthers; normal, yellowish in coloration and located above the pistils. Filaments: greenish and of irregular heights. Pistils: approximately 16 to 22 on average. Stigmas: normal, straw colored. Styles: free standing, dark fuchsine in coloration, of irregular heights. Receptacle: smooth, medium green, in longitudinal section it is in the shape of a pear.

Development:

*Vegetation.*—Very vigorous.

*Blooming.*—Very abundant.

*Resistance to diseases.*—Good.

*Aptitude to forcing.*—Good.

I claim:

1. A new and distinct variety of Floribunda rose plant characterized by the following combination of characteristics:

(a) forms in abundance attractive semi-double blossoms which are cardinal in coloration and exhibit an exceptionally long vase life, (b) exhibits a semi-erect growth habit, (c) exhibits vigorous vegetation, and (d) is particularly well suited for cut flower production;

substantially as herein shown and described.

* * * * *

MEICHEVIL